United States Patent [19]

Hanotier

[11] 4,278,810

[45] Jul. 14, 1981

[54] PROCESS FOR THE PREPARATION OF TEREPHTHALIC ACID

[75] Inventor: Jacques D. V. Hanotier, Lasne-Chapelle-Saint-Lambert, Belgium

[73] Assignee: Labofina S.A., Brussels, Belgium

[21] Appl. No.: 30,054

[22] Filed: Apr. 13, 1979

Related U.S. Application Data

[63] Continuation of Ser. No. 785,827, Apr. 8, 1977, abandoned, which is a continuation-in-part of Ser. No. 764,981, Feb. 2, 1977, abandoned.

[30] Foreign Application Priority Data

Oct. 26, 1976 [GB] United Kingdom ............... 44459/76

[51] Int. Cl.³ .......................................... C07C 51/255
[52] U.S. Cl. .................................................. 562/412
[58] Field of Search ............................... 562/412, 414

[56] References Cited

U.S. PATENT DOCUMENTS

| 2,892,864 | 6/1959 | Watson | 562/412 |
| 3,030,413 | 4/1962 | Taves | 562/412 |
| 3,883,584 | 5/1975 | Ichikawa | 562/412 |

*Primary Examiner*—Alan Siegel
*Attorney, Agent, or Firm*—Schwartz, Jeffery, Schwaab, Mack, Blumenthal & Koch

[57] ABSTRACT

There is disclosed a process for preparing terephthalic acid by oxidizing p-xylene which comprises contacting a substantially liquid mixture of p-xylene with p-toluic acid and water wherein the molar ratio of p-toluic acid to p-xylene is between about 0.01 and about 100 and the molar ratio of water to p-toluic acid is between about 0.4 and about 60, with a molecular oxygen-containing gas in the presence of an oxidation catalyst.

23 Claims, 1 Drawing Figure

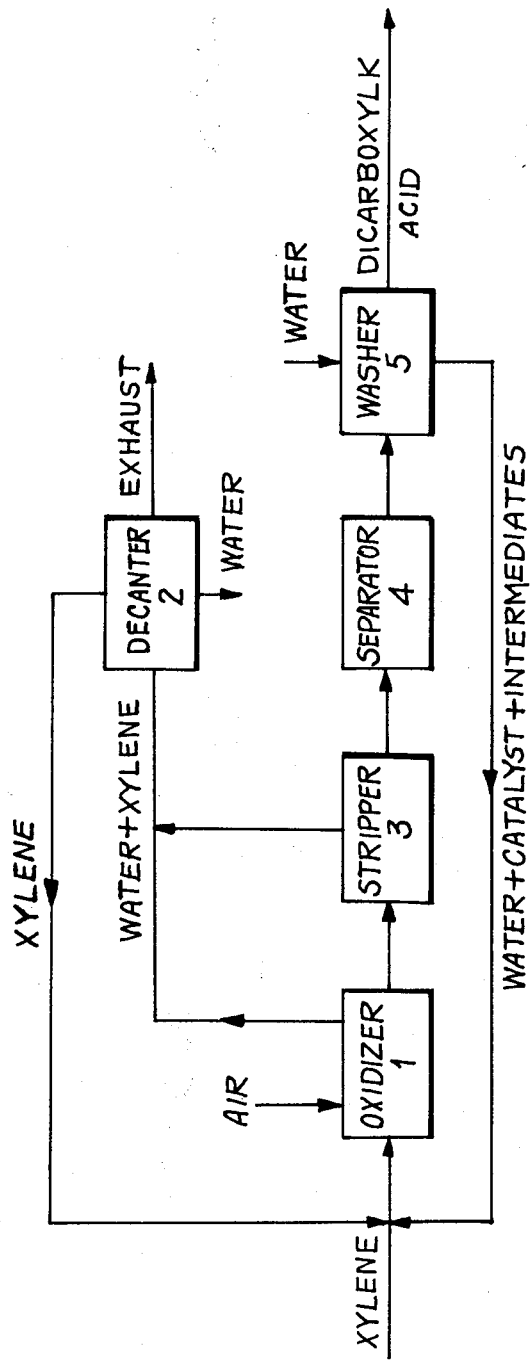

PROCESS FOR THE PREPARATION OF TEREPHTHALIC ACID

This is a continuation of application Ser. No. 785,827, filed Apr. 8, 1977, now abandoned, which in turn is a continuation-in-part of application Ser. No. 764,981 filed Feb. 2, 1977, also now abandoned.

BACKGROUND OF THE INVENTION

The present invention relates to a process for the preparation of terephthalic acid by oxidizing p-xylene in the liquid phase.

The oxidation of p-xylene into terephthalic acid in the liquid phase by molecular oxygen and in the presence of a heavy metal catalyst is a matter of considerable industrial importance and tremendous amount of work has been devoted to this problem over the past three decades. The major difficulty which is encountered when carrying out this operation results from the fact that, although p-xylene is easily transformed into p-toluic acid, the further oxidation of the latter is much more difficult and only negligible yields of terephthalic acid are obtained when ordinary catalytic processes are used. Numerous methods have been devised to overcome this difficulty, most of which consist in adding some activator or promoter. One of these methods comprises the use of a bromine-containing compound as an activator and a lower fatty acid, e.g., acetic acid, as a solvent. Although this method has reached full commercial fruition, it suffers serious drawbacks since the use of bromine at high temperatures raises severe corrosion problems which can only be solved by using expensive, highly corrosion-resistant equipment such as Hastelloy C or titanium. Moreover, under the strong oxidizing conditions applied in this process, the acetic acid solvent is significantly consumed which results in additional costs.

To avoid those corrosion problems, other methods have been proposed which consist in using as an activator, instead of bromine, an aldehydic and/or a ketonic compound, e.g., acetaldehyde and/or methylethylketone. These methods require less severe conditions and, although acetic acid is still used as a solvent, conventional stainless steel equipment can be employed. However, the activator is consumed in the reaction, mainly by oxidation into acetic acid which is therefore a co-product of the reaction and must be separated, purified and sold for the process to be economically attractive. Still other methods have been proposed to avoid the drawbacks arising from the use of an extraneous compound as an activator. For instance, it has been shown possible to oxidize in good yield p-xylene into terephthalic acid in an acetic acid medium containing only cobalt as a catalyst but in exceedingly large amounts. Nevertheless, in this case also, a significant consumption of acetic acid takes place.

More recently, different methods have been claimed whereby p-xylene is oxidized into terephthalic acid in the absence of any solvent and activator. Temperatures higher or close to the melting point of p-toluic acid, i.e., 179° C., are used in order to achieve liquid-phase conditions. Although these methods appear as being remarkably simple in their principle, they are difficult to apply in practice: without an activator the intermediate p-toluic acid is rather refractory to oxidation and without solvent, technical problems arise which are associated with the handling of solids and the removal of the reaction heat. For instance, the separation of terephthalic acid from the other components of the reaction mixture is a difficult task which is generally achieved by heating and washing treatments at elevated temperatures, e.g., at 230°–270° C. as is disclosed in U.S. Pat. No. 3,883,584 or even at 290°–350° C. as in U.S. Pat. No. 3,711,539. Obviously, such treatments require the use of expensive pressure vessels in corrosion-resistant materials and should cause increased decomposition and coloration of the reaction products.

SUMMARY OF THE INVENTION

It is an object of the present invention to provide a process for oxidizing p-xylene into terephthalic acid by which terephthalic acid is obtained in high yield and good purity.

It is a further object of the present invention to provide such a process which does not require highly corrosion-resistant equipment and can be effected in conventional stainless steel equipment.

It is a further object of the invention to provide such a process which can be performed in the absence of any additional solvent especially in the absence of additional lower fatty acids.

It is a further object of the invention to provide such a process which does not require the use of a promoter such as a bromine compound in addition to an oxidation catalyst.

It is a further object of the present invention to provide such a process wherein the terephthalic acid can easily be recovered from the oxidized reaction mixture at relatively moderate temperatures.

It is a further object of the present invention to provide such a process wherein the catalyst and oxidation intermediates can be recovered and re-used for oxidation.

It is a further object of the present invention to provide such a process wherein the temperature can easily be regulated by efficiently consuming the heat which evolves from the oxidation.

It is a further object of the invention to provide such a process which can be performed batchwise as well as continuously.

In order to accomplish the foregoing objects according to the present invention there is provided a process for preparing terephthalic acid by oxidizing p-xylene in a liquid phase which comprises the steps of (a) oxidizing a substantially liquid mixture essentially consisting of p-xylene, p-toluic acid and water wherein the molar ratio of p-toluic acid to p-xylene is between about 0.01 and about 100 and the molar ratio of water to p-toluic acid is between about 0.4 and about 60 with a molecular oxygen containing gas in the presence of an oxidation catalyst which consists of at least one heavy metal salt preferably a cobalt and/or manganese salt at oxidation conditions sufficient to form terephthalic acid and (b) recovering an oxidized mixture containing the terephthalic acid. The oxidation is preferably affected at a temperature of from about 140° to about 220° at a pressure sufficient to maintain at least part of the water in the liquid phase. From the oxidized mixture, solid terephthalic acid can be separated at a temperature sufficient to maintain the other components of this mixture in liquid solution, and the remaining portion of the mixture which contains oxidation intermediates and the catalyst may be reused for another oxidizing operation. The process may be effected batchwise or continuously, e.g., by introducing fresh p-xylene into the oxidizer at a rate sufficient to maintain an appropriate molar ratio between p-toluic acid p-xylene.

Further objects, features and advantages of the invention will become apparent from the detailed description of the invention and its preferred embodiments which follows when considered together with the accompanying drawing.

BRIEF DESCRIPTION OF THE DRAWING

The attached sheet of drawing represents a schematic flow diagram for a continuous process in accordance with the present invention.

DETAILED DESCRIPTION OF THE INVENTION

It is well known that in the oxidation of organic compounds by molecular oxygen, the presence of water is generally not desirable and may even be detrimental. According to the most widespread opinion, water would interfere with the radical initiation processes of the reaction. For instance, in U.S. Pat. No. 2,853,514 dealing with the oxidation of alkylbenzenes and more especially of p-xylene, it is stated that "the water concentration should be maintained at less than 3 molar in order to avoid an unreasonable prolonged induction period". Expressed in other terms, the water concentration should be maintained at less than about 5% by weight. It is only when a powerful radical-generating species such as bromine is present in the system that water may be tolerated in substantial amounts. However, even in such cases, it appears that water is inherently detrimental for oxidation reactions. Thus, in U.S. Pat. No. 3,139,459 which discloses a process for oxidizing p-xylene into terephthalic acid in the presence of a cobalt catalyst, HBr and of acetic acid as a solvent, it is taught that "when an amount of water in excess of about 0.05 parts by weight per part of solvent (5 percent by weight) is allowed to accumulate, the reaction is substantially stopped". Accordingly, in view of the prior art teachings it is highly surprising that under the conditions of the present process not only may water be used without prejudice for the reaction in quantities in excess of 50 wt % or even more, but also, as shown hereinafter, that water must be present in substantial amounts for the reaction to take place smoothly without induction or inhibition problems.

The amount of water to be used in the process of the present invention depends on different factors, mainly on the working temperature and the composition of the reaction mixture. Preferably, the amount of water will be sufficient for p-toluic acid to be substantially in solution at the working temperature. As the solubility of p-toluic acid in water steeply increases with a temperature increase within the range which is considered here, the amount of water to be used may be reduced when the temperature is increased. As a general rule, however, the molar amount of water will not be lower than 0.4 mole per mole of the p-toluic acid which is present in the reaction mixture.

For practical reasons, it is often advantageous to work with quantities of water higher than these which are needed for keeping the p-toluic acid in solution. For instance, if relatively large amounts of terephthalic acid (resulting from the oxidation reaction) are present in the system, enough water may be added so that a workable slurry is obtained. However, there is no advantage in using such a high amount of water that more than, e.g., 10%, of the terephthalic is dissolved at the working temperature. Otherwise stated, water should not exceed a molar amount of 160,000 10-0.0175 T per mole of terephthalic acid, T being the working temperature in °C. But it has been found that still other factors have to be taken into account. For example, when the amount of terephthalic acid in the system is relatively high, more especially when the molar ratio of terephthalic acid to p-toluic acid is higher than ⅔, the upper limit as defined hereinabove may be too high for the oxidation reaction to take place at a high rate. As a matter of fact, the presence of a too large amount of water with respect to p-toluic acid may affect adversely the reaction rate, especially when the amount of p-xylene in the system is relatively small as it is the case when the reaction has reached an advanced stage. Preferably, the amount of water will be lower than 60 moles per mole of p-toluic acid and in most cases there is no advantage in using an amount of water substantially higher than 10 moles per mole of the p-toluic acid which is present in the system.

The temperature at which the oxidation reaction has to be carried out is not critical either but, as a general rule, it is comprised between 140° and 220° C. Below 140° C., the solubility of p-toluic acid in water is too small for allowing to take full advantage of the use of water in accordance with the present invention. On the other hand, working above 220° C. would result in increased overoxidation, undesirable side reactions and severe corrosion problems. Preferably, the reaction temperature may vary between 160° and 190° C.

The catalyst which is used in the process of the present invention may be any salt of a heavy metal which is conventionally employed in the oxidation of p-xylene into terephthalic acid provided that it can be dissolved in the reaction medium or reacted with a component of the reaction mixture to become soluble. The salts of many aliphatic carboxylic acids may be used such as the acetates, proprionates, stearates, naphthenates and the like. Obviously, when such salts are added in a system comprising large amounts of p-toluic acid, anion exchange readily takes place with formation of the corresponding toluate which becomes therefore the effective catalyst. Particularly efficient catalysts for the process of the invention are the salts of cobalt and manganese, used alone or in admixture. Here again, the different operating variables are tightly interrelated and, for optimum activity, the catalyst has to be chosen in consideration of the other conditions. For instance, cobalt salts are especially efficient in systems containing a large amount of unreacted p-xylene and a relatively small amount of water. By contrast, manganese salts are particularly useful in systems wherein a large amount of water is present. In most cases, however, the best catalytic effects are obtained with a combination of both manganese and cobalt. The amount of catalyst to be used may be varied within large limits but, as a general rule, the total concentration thereof will be comprised between 0.001 and 0.1 M on a water-free base, i.e., in mole per liter of organic material present in the system.

When p-xylene, water and catalyst are brought into contact and heated at a temperature in the range as indicated in the presence of molecular oxygen, active oxidation does not readily take place unless p-toluic acid is also present in the system. This is surprising in consideration of the fact that the latter is much less easily oxidized by molecular oxygen than p-xylene. Moreover, if p-toluic acid is present but in too small amounts, oxidation takes place actively for some time but then falls abruptly down to a negligible level. This phenomenon is the more marked as more water and less manganese catalysts are present in the system. Accordingly, it is an important aspect of the present invention that p-toluic acid must at any time be present in the reaction mixture in sufficient amounts. Conveniently this amount is such that the molar ratio of p-toluic acid to p-xylene is at least 0.01.

In carrying out the process of the present invention, p-xylene in admixture with p-toluic acid and eventually other intermediate oxidation products is heated in the presence of water and the heavy metal catalyst while an oxygen-containing gas is passed through the mixture. Efficient stirring is provided so as to ensure intimate contact between the different components. Active oxidation soon takes place as attested by an intense oxygen absorption and by a rapid increase of temperature. An important advantage of the present process is the ease whereby temperature control can be achieved: owing to the presence of a substantial amount of water in the reaction mixture, the heat evolved from the highly exothermic oxidation can easily be removed by controlled evaporation of water.

As the reaction proceeds, i.e., as more p-xylene is transformed, the oxygen absorption decreases and may even virtually cease if additional p-xylene is not added into the system. Indeed, it is another important aspect of the present invention that in order to ensure a vigorous oxidation and high yields in terephthalic acid, it is required that p-xylene be present in the system in such an amount that the molar ratio of p-toluic acid to p-xylene does not become higher than 100. Accordingly, in the practice of the invention, fresh p-xylene should be added to the reaction mixture at such a rate as to maintain this condition fulfilled. This addition may be made continuously or intermittently. For instance, the reaction may be performed strictly in batch until oxygen absorption has virtually ceased. Then, terephthalic acid can be separated by simple filtration at the reaction temperature or at least at a temperature at which p-toluic acid is kept in solution. Indeed, it is an important practical advantage of the present process that the terephthalic acid which is formed in the reaction is present as relatively large crystals which are suspended in an aqueous medium wherein the major part of the intermediate p-toluic acid is dissolved. It can therefore be easily separated from the latter by filtration, centrifugation or any solid-liquid separation device at any temperature at which p-toluic acid is still substantially in solution. The filtrate from this operation contains the catalyst in addition to substantially the whole of the intermediate oxidation products; it can therefore be reused as such, together with fresh p-xylene, for another operation.

According to another embodiment of the present invention, the process is carried out continuously as illustrated schematically by the enclosed flow sheet. The reaction is performed in an oxidizer 1. The heat which evolves during the reaction is removed by vaporizing some of the water from the reaction mixture. Some p-xylene is vaporized azeotropically along with the water and is separated therefrom in the decanter 2 after condensation of the vapors. The oxidation product from the oxidizer 1 is transferred into a stripper 3 wherefrom any unreacted p-xylene is removed by stripping with water. Terephthalic acid which is present as a precipitate in the effluent from the stripper 3 is separated in a separator 4 and washed in a washer 5 with hot water which may at least in part come from the decanter 2. The filtrate and washings are directly recycled to the oxidizer 1. As those skilled in the art will appreciate, it is an especially advantageous feature of this process that the water which is used as a washing solvent for the terephthalic acid may be heated and vaporized, at least in part, by the heat which evolves during the oxidation itself, without need of an extraneous source of energy.

Obviously, various modifications can be brought to the above-described procedures without departing from the scope of the present invention which will now be described with reference to the following examples.

EXAMPLE 1

Into a corrosion-resistant autoclave of one-liter capacity equipped with a mechanical agitation device, a heating jacket, a condenser, a gas inlet tube and a vent, there is charged:

| | |
|---|---|
| p-xylene | 100 g |
| p-toluic acid | 180 g |
| water | 50 g |
| cobalt naphthenate | 7.5 millimoles (about 0.025 mole per liter of organic material). |

The molar ratio of p-toluic acid to p-xylene and of water to p-toluic acid are 1.4 and 2.1, respectively.

The reactor is pressurized with air up to a pressure of 20 atmospheres and the above mixture is heated while stirring and introducing air at a flow rate of 300 liters per hour (measured at 20° C. and atmospheric pressure). Oxygen absorption starts when the temperature reads about 100° C. Temperature then increases rapidly and is maintained at 185° C. by controlled cooling. The oxygen absorption rate increases steeply during the first 20 minutes of the reaction and then decreases progressively. After 240 minutes of reaction, 101 liters of oxygen have been absorbed. The reaction is then discontinued by cooling and the autoclave is opened. The precipitate contained therein is washed with water, filtered and dried under vacuum at about 80° C. The filtrate is treated with a cation-exchange resin to remove the metal catalysts and then evaporated to dryness.

The analyses of the different fractions are made by a combination of acidimetry, polarography and vapor-phase chromatography. The reaction mixture is thus shown to consist of 137 g of terephthalic acid, 177 g of p-toluic acid and 7 g of p-carboxybenzaldehyde. During the reaction, about 3 g of p-xylene have been entrained by the air flow. Thus, under the conditions of the present invention, not only p-xylene is transformed into p-toluic acid but, simultaneously, the latter is transformed extensively into terephthalic acid.

EXAMPLE 2

Into the same autoclave as in the preceding example, there is charged:

| | |
|---|---|
| p-xylene | 100 g |
| p-toluic acid | 180 g |
| water | 150 g |
| cobalt naphthenate | 7.5 millimoles |
| manganese naphthenate | 0.75 millimole |

Thus, the same molar ratio of p-toluic acid to p-xylene is used as in the preceding example but here the water to p-toluic acid ratio is 6.3 instead of 2.1 and some manganese salt is added. Evident oxygen absorption starts when the temperature reaches about 140° C. As in the preceding example, the temperature is maintained at 185° C. After about 295 minutes of reaction, 106 liters of oxygen have been absorbed and the reaction is discontinued by cooling. The reaction mixture is then treated and analyzed as in the preceding example. It consists of 182 g of terephthalic acid, 118 g of p-toluic acid, i.e., markedly less than initially charged, and 7 g of carboxybenzaldehyde.

A comparative experiment is carried out under the same conditions except that the manganese naphthenate is omitted. Evident oxygen absorption starts as hereinabove but suddenly falls off after about 80 minutes of reaction. Total oxygen absorption is limited to 58 liters and the amount of terephthalic acid in the reaction mixture is only 68 g. These results show the advantage of using at least a certain amount of manganese salt together with cobalt salt as catalyst for oxidizing p-xylene into terephthalic acid when the reaction is carried out in the presence of substantial amounts of water.

EXAMPLE 3

The experiment of Example 2 is repeated except that the oxidation is discontinued after heating for about 120 minutes at 185° C. Then the reaction mixture is discharged on a pressure filter which is heated at the same temperature whereby the terephthalic acid is separated from the bulk of the other oxidation products. The resulting cake is washed twice with water at 185° C. and dried. After cooling at room temperature, the filtrate and washings are filtered again to separate precipitated p-toluic acid which is also washed with water. The final filtrate containing substantially the water. The final filtrate containing substantially the whole of the catalysts and some p-toluic acid is evaporated to dryness. The resulting residue is charged into the autoclave together with the precipitate of p-toluic acid and the same amounts of fresh p-xylene and water as in the original charge. The resulting mixture is then oxidized as already described.

The same procedure is repeated nine times. Upon analysis it is concluded that the average yield of the terephthalic acid produced in this series of operations is 87 mole percent based on the amount of p-xylene reacted.

EXAMPLE 4

The experiment of Example 2 is repeated except that 7.5 millimoles of manganese naphthenate are used as the sole catalyst. After 310 minutes of reaction, 95 liters of oxygen have been absorbed. The reaction mixture is then cooled, treated and analyzed as described in Example 1. It consists of 150 g of terephthalic acid, 146 g of p-toluic acid and 7 g of p-carboxybenzaldehyde.

EXAMPLE 5

The experiment of Example 2 is repeated except that 75 ml of water are charged into the autoclave and that 7.5 millimoles of manganese toluate are used as the sole catalyst. After 240 minutes of reaction 81 liters of oxygen have been absorbed. Upon analysis, the reaction mixture was shown to consist of 111 g of terephthalic acid, 179 g of p-toluic acid, i.e., almost the same amount as in the initial charge, 7 g of carboxybenzaldehyde and some unreacted p-xylene. Thus, in summary, the overall result of the operation is a transformation of p-xylene into terephthalic acid in the presence of an almost steady concentration of p-toluic acid.

EXAMPLE 6

The same amounts of p-xylene, p-toluic acid and water as in Example 2 are charged into the autoclave together with 3.75 millimoles of each cobalt and manganese naphthenates. The mixture is then oxidized by air under exactly the same conditions as in Example 2 except that the temperature is 170° C. instead of 185° C. After 230 minutes of reaction 74 liters of oxygen have been absorbed. The reaction mixture is then cooled, treated and analyzed as described in Example 1. It consists of 98 g of terephthalic acid, 179 g of p-toluic acid, 7 g of p-carboxybenzaldehyde and some unreacted p-xylene.

EXAMPLE 7

Under the conditions of the preceding example, a series of 13 consecutive operations are carried out thereby recycling the catalysts and intermediates as described in Example 3. Terephthalic acid is obtained as a white powder in an average yield of 87 mole percent. From a thorough analysis of the different streams, it is concluded that the remainder consists mainly of carbon dioxide, some p-tolualdehyde not recycled and some light acids. No formation of heavy by-products, tar or other colored bodies is detected.

EXAMPLE 8

The same amounts of p-xylene, p-toluic acid and water as in Example 2 are charged into the autoclave together with 3.9 millimoles of each cobalt and manganese acetates. The mixture is then oxidized by air under exactly the same conditions as in Example 2 except that the temperature is 165° C.

After 300 minutes of reaction, 61 liters of oxygen have been absorbed and upon analysis of the reaction mixture it is shown that 91 g of terephthalic acid have been formed.

This example shows that by the process of the present invention p-xylene can be transformed into terephthalic acid at a temperature well below the melting point of p-toluic acid without resorting to the use of a lower fatty acid solvent.

EXAMPLE 9

The following charge is heated while stirring and passing air thereinto at a flow rate of 300 liters per hour under a pressure of 20 atmospheres:

| | |
|---|---|
| p-xylene | 68 g |
| p-toluic acid | 120 g |
| water | 250 g |
| cobalt naphthenate | 2.5 millimoles |
| manganese naphthenate | 10.0 millimoles |

Thus, the water to p-toluic acid molar ratio is 15.7 instead of 6.3 as in most of the preceding examples. Oxygen absorption starts when the temperature reaches about 125° C. The temperature is then maintained at 170° C. After 300 minutes of reaction, 43 liters of oxygen have been absorbed and the reaction is discontinued by cooling. The reaction mixture is then treated and analyzed as described in Example 1. It comprises 49 g of terephthalic acid, 139 g of p-toluic acid and 5 g of p-carboxybenzaldehyde.

This example clearly shows that the oxidation of p-xylene into terephthalic acid can be carried out in the presence of very large amounts of water in accordance with the process of the present invention.

EXAMPLE 10

The experiment of the preceding example is repeated except that p-xylene is omitted and that manganese naphthenate is used as the sole catalyst. Only negligible absorption of oxygen is observed upon heating the mixture at 170° C. for one hour. The temperature is then raised up to 185° C. but no change in the absorption rate takes place. After one hour at the latter temperature 50 ml of p-xylene are injected into the reactor. Evident oxygen absorption then suddenly starts and after 145 minutes amounts to 29 liters.

This example shows that under the conditions of the present process p-toluic acid cannot be oxidized into terephthalic acid if p-xylene is not also present in the system.

EXAMPLE 11

The following charge is heated while stirring and passing air thereinto at a flow rate of 200 liters per hour under a pressure of 20 atmosphere:

| | |
|---|---|
| p-xylene | 155 g |
| p-toluic acid | 10 g |
| water | 50 g |
| cobalt naphthenate | 2.5 millimoles |
| manganese naphthenate | 2.5 millimoles |

Thus, the molar ratios of p-toluic acid to p-xylene and of water to p-toluic acid are 0.05 and 38, respectively. Intense oxygen absorption starts when the temperature reaches 180° and amounts to 92 liters after 245 minutes at 185° C., when the reaction is discontinued by cooling. As is shown by analysis, the reaction mixture consists of 96 g of terephthalic acid, 108 g of cf p-toluic acid and 5 g of p-carboxybenzaldehyde.

A comparative experiment is carried out under the same conditions except that the p-toluic acid is omitted. No significant reaction takes place while heating the mixture for 4 hours at 185° C.

In another comparative experiment, 100 g of water are charged into the autoclave instead of 50 g. Therefore, the molar ratio of water to p-toluic acid is 76 instead of 38. Evident oxygen absorption starts as the temperature reaches 175° C. However, after about 75 minutes of reaction at 185° C., the oxygen absorption rate falls suddenly down to a negligible level. The total oxygen absorption is only 44 liters.

These comparative experiments show how important it is to have enough p-toluic acid relative to the amount of water in the system in order to be able to oxidize p-xylene into terephthalic acid according to the process of the present invention.

EXAMPLE 12

The following charge is heated while passing air thereinto at a flow rate of 300 liters per hour under a pressure of 20 atmospheres:

| | |
|---|---|
| p-xylene | 100 g |
| p-toluic acid | 180 g |
| cobalt naphthenate | 3.75 millimoles |
| manganese naphthenate | 3.75 millimoles. |

It can be seen that this charge is the same as in the experiment of Example 6 except that water is omitted. Oxygen absorption starts as the temperature reaches about 160° C. but falls rapidly to almost nill after an absorption of only 4.5 liters. Heating is continued for two hours at 185° C. without any effect upon the reaction rate. Then 30 ml of water are injected into the reactor whereby intense oxygen absorption takes place abruptly. Heating at 185° C. is still continued for 240 minutes before cooling the reaction mixture which is treated and analyzed as already described. It is thus determined that the reaction mixture consists of 143 g of terephthalic acid, 179 g of p-toluic acid and 7 g of p-carboxybenzaldehyde.

This example shows that under the conditions of the present process not only water is not detrimental for the oxidation of p-xylene but exerts a beneficial effect upon the initiation thereof.

What is claimed is:

1. A process for producing terephthalic acid comprising the steps of:
   providing a substantially liquid, aqueous mixture consisting essentially of p-xylene, p-toluic acid and a solvent consisting essentially of water wherein the molar ratio of p-toluic acid to p-xylene is between about 0.01 and about 100, the molar ratio of water to p-toluic acid is between about 0.4 and about 60, the initial water content of said mixture is at least 5 weight percent and the amount of water is at least sufficient to maintain the p-toluic acid in solution at the reaction temperature;
   oxidizing said mixture with a molecular oxygen-containing gas at oxidation conditions and in the presence of an oxidation catalyst comprising at least one heavy metal salt to produce terephthalic acid as the principal product of the oxidation reaction; and
   separating terephthalic acid from the oxidized mixture.

2. The process as defined by claim 1 wherein the oxidation catalyst consists of at least one salt selected from the group of cobalt and manganese salts.

3. The process as defined by claim 1 wherein the oxidation step is effected at a temperature of from about 140° C. to about 220° C. and at a pressure sufficient to maintain at least part of the water in the liquid phase at the reaction temperature.

4. The process as defined by claim 2 wherein the amount of oxidation catalyst is comprised between about 0.001 mole and about 0.1 mole per liter of organic material present in the system.

5. The process as defined by claim 1 wherein the molar ratio of water to p-toluic acid is between about 0.4 and about 10.

6. The process as defined by claim 3 wherein the reaction temperature is in the range of from 160° to 190° C.

7. The process as defined by claim 1 wherein the heavy metal salt is an organic acid salt which dissolves in the reaction mixture.

8. The process as defined by claim 2 wherein the oxidation catalyst is a cobalt salt.

9. The process as defined by claim 2 wherein the oxidation catalyst is a manganese salt.

10. The process as defined by claim 2 wherein the oxidation catalyst is a mixture of cobalt salts and manganese salts.

11. The process as defined by claim 1 wherein the liquid mixture contains between about 5 and about 50 weight % of water.

12. The process as defined by claim 5 wherein the molar ratio of water to p-toluic acid is between about 3 and about 10.

13. The process as defined by claim 1 wherein said separating step further comprises separating from said oxidized mixture solid terephthalic acid at a temperature sufficient to maintain the other components of the oxidized mixture in a liquid solution.

14. The process as defined by claim 13 which further comprises the steps of recovering from the oxidized mixture an aqueous mixture containing the catalyst and intermediate oxidation products mixing said aqueous mixture with fresh p-xylene and oxidizing the resulting mixture.

15. The process as defined by claim 1 wherein the oxidizing step further comprises evaporating sufficient water to consume the heat which evolves during the oxidation.

16. The process as defined by claim 1 wherein the oxidizing step is performed in an oxidizer and further comprises the step of introducing fresh p-xylene into the oxidizer at a rate sufficient to maintain said molar ratio between p-toluic acid and p-xylene.

17. The process as defined by claim 16 wherein the oxidizing step further comprises the steps of evaporating an azeotropic mixture of water and p-xylene;

introducing the azeotropic mixture into a decanter;

recycling p-xylene from the decanter into the oxidizer; and the recovering step further comprises the steps of introducing the oxidized mixture into a stripper stripping the oxidized mixture with water removing a mixture of unreacted p-xylene and water from the stripper and introducing it into the decanter then introducing the oxidized mixture into a separator separating solid terephthalic acid from the oxidized mixture at a temperature sufficient to maintain the other components of the oxidized mixture in liquid solution;

washing the terephthalic acid with hot water; and recycling the said liquid solution and the washing water into the oxidizer.

18. The process as defined by claim 17 wherein at least part of the hot water is recovered from the decanter.

19. The process as defined by claim 1, wherein said substantially liquid mixture is substantially free of any lower fatty acids and halogen compounds.

20. The process of claim 1, wherein terephthalic acid is produced in the form of solid crystals and the separation step is effected by mechanically removing said crystals from the oxidized mixture while maintaining the other components of said mixture in the liquid phase.

21. The process of claim 1, wherein the oxidation reaction is effected at a temperature between about 140° C. and about 220° C., further comprising removing excess heat produced during the oxidation reaction by controlled evaporation of water from the mixture, and carrying out the oxidation reaction at an elevated pressure sufficient to maintain at least part of the water in the liquid phase at the reaction temperature.

22. The process of claim 1, wherein the mole ratio of water to p-toluic acid is at least 3.

23. The process of claim 1 further comprising agitating said mixture during the oxidation reaction to maintain intimate contact between the components of the mixture wherein terephthalic acid is produced as an aqueous slurry of terephthalic acid crystals.

* * * * *